US00PP35635P2

(12) United States Plant Patent
Postill

(10) Patent No.: US PP35,635 P2
(45) Date of Patent: Feb. 6, 2024

(54) ***PHILADELPHUS* PLANT NAMED 'W1'**

(50) Latin Name: ***Philadelphus* sp.**
Varietal Denomination: W1

(71) Applicant: Alan Postill, Hampshire (GB)

(72) Inventor: Alan Postill, Hampshire (GB)

( * ) Notice: Subject to any disclaimer, the term of this patent is extended or adjusted under 35 U.S.C. 154(b) by 0 days.

(21) Appl. No.: 18/118,361

(22) Filed: Mar. 7, 2023

(51) Int. Cl.
*A01H 5/00* (2018.01)
*A01H 6/48* (2018.01)

(52) U.S. Cl.
USPC ..... Plt./226

(58) Field of Classification Search
USPC ..... Plt./226
See application file for complete search history.

(56) References Cited

PUBLICATIONS

CPVO Register—Application Consultation—version 4.9.14; citation for 'W1' (Retrieved from the Internet on Jun. 26, 2023).*

* cited by examiner

*Primary Examiner* — Susan McCormick Ewoldt
(74) *Attorney, Agent, or Firm* — Cassandra Bright

(57) ABSTRACT

A new and distinct *Philadelphus* cultivar named 'W1' is disclosed, characterized by a compact habit, and large, clear white flowers with a strong, sweet scent. The new variety is a *Philadelphus*, normally used for outdoor ornamental purposes.

2 Drawing Sheets

Figure 1:
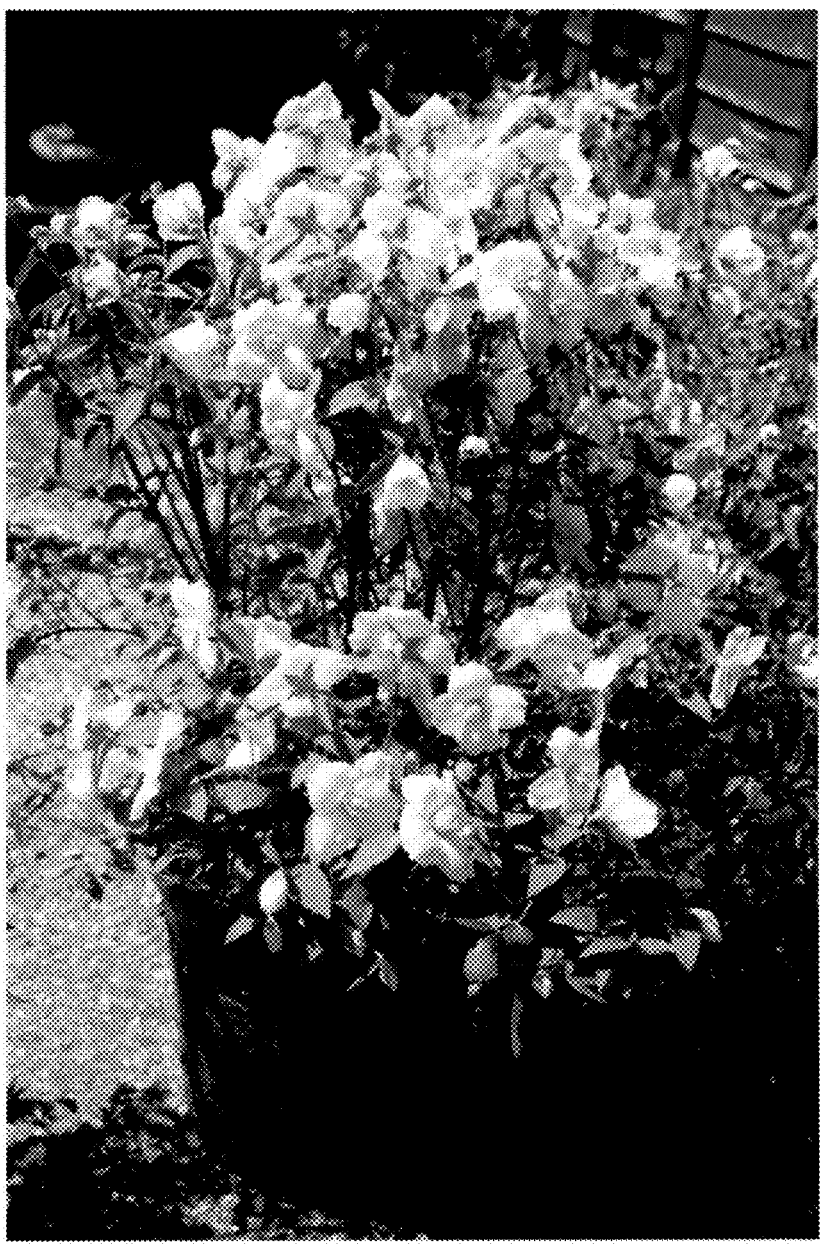

Latin name of the genus and species: *Philadelphus* sp.
Variety denomination: 'W1'.

BACKGROUND OF THE INVENTION

The new *Philadelphus* cultivar is a product of a planned breeding program conducted by the inventor in Hampshire, United Kingdom. The objective of the breeding program was to develop large flowers with a nice, strong scent, and clear white flower color. The open-pollination resulting in this new variety was made during 2014.

The seed parent is the unpatented variety *Philadelphus maculatus* 'Sweet Clare'. The pollen was taken from several unnamed, unpatented proprietary *Philadelphus* seedlings. The new variety was selected in 2018 by the inventor in a group of seedlings resulting from the 2014 crossing, in a nursery in Hampshire, United Kingdom.

Asexual reproduction of the new cultivar was performed by softwood cuttings. This was first performed at the same nursery in Hampshire, United Kingdom in 2018, and has shown that the unique features of this cultivar are stable and reproduced true to type in multiple successive generations.

SUMMARY OF THE INVENTION

The cultivar 'W1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'W1' These characteristics in combination distinguish 'W1' as a new and distinct *Philadelphus* cultivar:

1. Relatively large flowers.
2. Clear white flowers.

3. Compact size.
4. Floriferous.
5. Strong, pleasant floral scent.

PARENT COMPARISONS

Plants of the new cultivar 'W1' are similar to plants of the seed parent in most horticultural characteristics; however, plants of the new cultivar 'W1' differ in the following;

1. Flowers of the new variety are on average 3.2 cm in diameter; flowers of the seed parent are on average 2.5 cm in diameter.
2. Flower color of the new variety is fully white, while flower color of the seed parent is white with a pink heart.
3. Fragrance of the new variety is more pleasant than the fragrance of the seed parent.

The exact pollen parent cannot be identified.

COMMERCIAL COMPARISONS

Plants of the new cultivar 'W1' are comparable to the commercial variety *Philadelphus* 'Belle Etoile', unpatented. The two *Philadelphus* varieties are similar in most horticultural characteristics; however, the new variety 'W1' differs in the following;

1. Flowers of the new variety are fully white, while flowers of this comparator are white with pink centers.

Plants of the new cultivar 'W1' are comparable to the commercial variety *Philadelphus* 'Snowwhite Fantasy', U.S. Plant Pat. No. 13,774. The two *Philadelphus* varieties are similar in most horticultural characteristics; however, the new variety 'W1' differs in the following;

1. Flowers of the new variety are single, while flowers of this comparator are double.
2. Flowers of the new variety have fewer petals than flowers of this comparator.

3. Leaves of the new variety are smaller than leaves of this comparator.

Plants of the new cultivar 'W1' are comparable to the commercial variety *Philadelphus* 'Dainty Lady', U.S. Plant Pat. No. 24,536. The two *Philadelphus* varieties are similar in most horticultural characteristics; however, the new variety 'W1' differs in the following;

1. Petals of the new variety are more rounded and overlapping than petals of this comparator.
2. Sepal color of the new variety is green, while sepal color of this comparator is purple.

Plants of the new cultivar 'W1' are comparable to the commercial variety *Philadelphus* 'P1', plant patent application number 18/118,353. The two *Philadelphus* varieties are similar in most horticultural characteristics; however, the new variety 'W1' differs in the following;

1. Petals of the new variety are more rounded and overlapping than petals of this comparator.
2. Petals of 'W1' are more reflexed back than petals of 'P1'.
3. Petals of 'W1' are white, petals of 'P1' are white with pink.

BRIEF DESCRIPTION OF THE PHOTOGRAPHS

The accompanying photograph in FIG. 1 illustrates in full color a typical plant of 'W1' in a 23 cm pot. Age of the plant photographed is approximately 3 years old from a rooted cutting.

Figure 2:
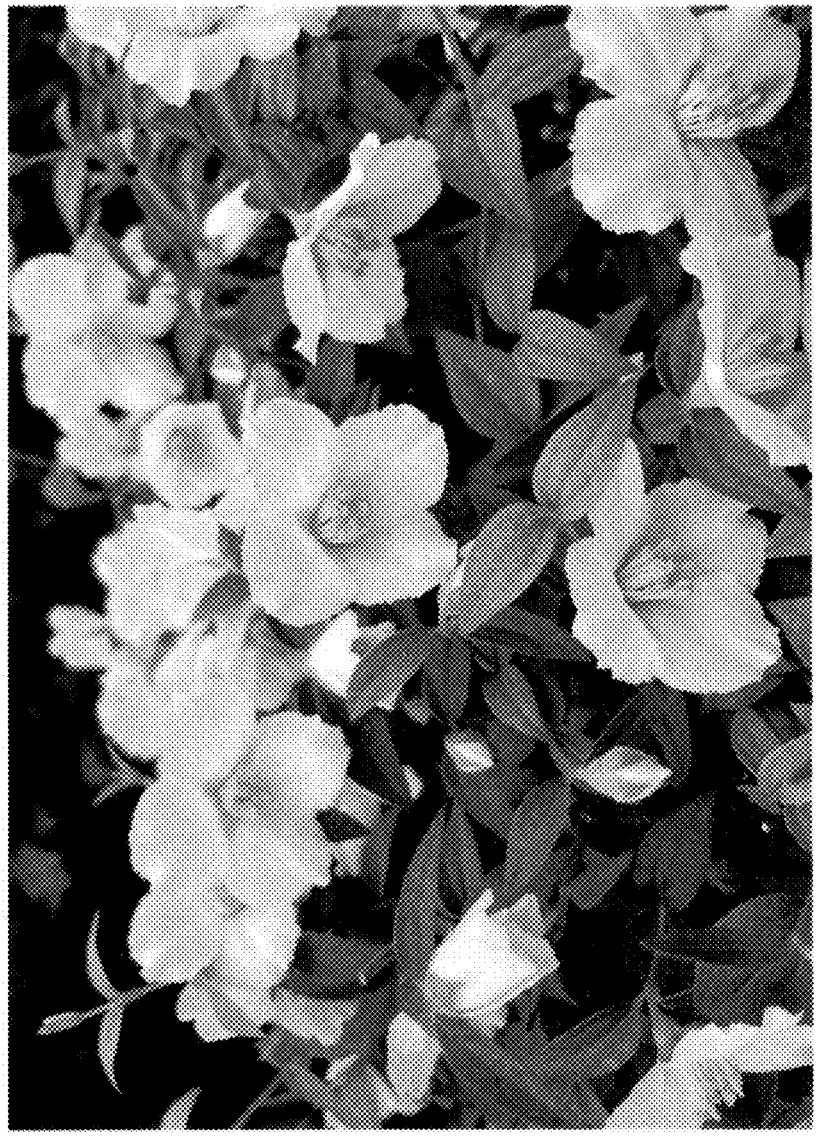

FIG. 2 illustrates a close up view of typical flowers of 'W1'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'W1' plants grown outdoors in Waddinxveen, the Netherlands. The growing temperature ranged from approximately 18° C. to 27° C. during the day and from approximately 5° C. to 10° C. during the night. General light conditions are normal sunlight and numerical values represent averages of typical plant types.

Botanical classification: *Philadelphus* sp. 'W1'.

PROPAGATION

Type of propagation typically used: Hardwood cuttings.
Time to initiate roots: Soft cuttings: 2 weeks; Hard cuttings: 6 to 8 weeks.
Time to produce a rooted cutting: 1 year from rooted plug.
Root description: Dense.

PLANT

Age of plant described: 3 years old.
Container size: 23 cm container.
Plant type: Woody shrub.
Growth habit: Upright, outward spreading.
Plant spread: 78 cm.
Plant height: 62 cm.
Branching habit: Free branching.
Length of primary lateral branches: 30 cm.
Diameter of lateral branches: 2 mm.
Stem:
- *Color*.—Young branches: RHS Yellow-Green 145A. Mature branches: RHS Brown 199C, maturing more towards 199A.
- *Strength*.—Moderately strong.
- *Length*.—Average range 40 to 70 cm, unpruned.
- *Width*.—Average 5 to 9 mm.
- *Surface*.—Smooth, glabrous.

Internode length: Average 3 cm.

FOLIAGE

Leaf:
- *Arrangement*.—Single, opposite.
- *Length*.—Average range 2.5 cm to 3.5 cm. Longest foliage 4.5 cm.
- *Width*.—Average range 1.5 cm to 1.8 cm. Widest foliage 2.3 cm.
- *Shape of blade*.—Ovate to narrow ovate.
- *Apex*.—Acute.
- *Base*.—Obtuse.
- *Margin*.—Young Leaves: Entire. Mature Leaves: Serrated (8 teeth per leaf).
- *Surface*.—Slightly rugose, pubescent.
- *Color*.—Young foliage upper side: RHS Green 137A. Young foliage under side: RHS Green 137C. Mature foliage upper side: Near RHS Green 137C. Mature foliage under side: Near RHS Green 137C.
- *Venation*.—Pattern: Pinnate. Venation color upper side: RHS Green 137A. Venation color under side: RHS Green 137C.
- *Petiole*.—Length: 3 mm. Diameter: 1 mm. Color: RHS Yellow-Green 144B.

FLOWER

Natural flowering season: Late May and June, reblooms in summer.
Flowers per lateral stem: Up to 14 flowers per branch.
Flowers buds per plant: 20 buds per branch.
Individual flowers:
- *Shape*.—Rotate.
- *Type*.—Single.
- *Diameter*.—3.2 cm.
- *Depth*.—1.5 cm.
- *Aspect*.—Outwardly facing.
- *Persistence*.—Self-cleaning.
- *Fragrance*.—Strong and sweet.

Petals:
- *Arrangement*.—Cruciform, overlapping.
- *Number*.—4.
- *Shape*.—Broadly ovate.
- *Margin*.—Entire with slight ruffled undulation.
- *Apex*.—Rounded.
- *Base*.—Attenuate.
- *Length*.—1.5 cm.
- *Width*.—1.3 cm.
- *Texture*.—Pubescent.
- *Color*.—Upper surface: RHS White 155C. Under surface: RHS White 155C.

Bud:
- *Shape*.—Ovoid.
- *Size*.—About 1 cm.
- *Color*.—RHS White 155C.

Sepals:
*Arrangement*.—Cruciform.
*Shape*.—Elliptic.
*Apex*.—Aristate.
*Base*.—Fused, enclosing ovary.
*Margin*.—Entire.
*Quantity per flower*.—4.
*Length*.—0.8 cm.
*Width*.—0.3 cm.
*Texture*.—Pubescent.
*Color*.—Upper: RHS Yellow-Green 144A. Lower: RHS Yellow-Green 144A.

Peduncle:
*Length*.—Between 3 and 8 mm.
*Diameter*.—1 mm.
*Texture*.—Pubescent.
*Angle*.—Straight on top of branches.
*Color*.—RHS Green 144A.
*Strength*.—Strong.

Pedicel: None.
Petaloids: None.

REPRODUCTIVE ORGANS

Stamens:
*Number*.—About 34.
*Filament length*.—About 5 mm.
*Filament color*.—RHS White 155A.

Anthers:
*Shape*.—Linear, basifixed.
*Length*.—1 mm.
*Color*.—Near RHS Yellow-Green 152D.
*Pollen amount*.—Low.
*Pollen color*.—RHS Yellow 9A.

Pistil:
*Number*.—4, fused.
*Length*.—5 mm.
*Style*.—Length: 3 mm. Color: RHS White 155D.

Stigma:
*Shape*.—Oblong.
*Length*.—2 mm.
*Color*.—RHS Yellow 4D.
*Ovary color*.—RHS White 155D.

OTHER CHARACTERISTICS

Fruits and seeds: Not observed to date.
Disease/pest resistance: Neither resistance nor susceptibility to normal diseases and pests of *Philadelphus* observed.
Temperature range: Winter hardy to −15° C.

What is claimed is:

1. A new and distinct cultivar of *Philadelphus* plant named 'W1' as herein illustrated and described.

* * * * *